(12) United States Patent
Vainio et al.

(10) Patent No.: US 10,058,538 B2
(45) Date of Patent: Aug. 28, 2018

(54) COMPOSITIONS COMPRISING SUBSTITUTED BENZOFUROQUINOLIZINE AND $\alpha_2$-ADRENERGIC AGONISTS

(71) Applicant: VETCARE OY, Salo (FI)

(72) Inventors: Outi Vainio, Turku (FI); Marja Raekallio, Helsinki (FI); Juhana Honkavaara, Helsinki (FI); Flavia Restitutti, Helsinki (FI); Heta Turunen, Hámeenlinna (FI)

(73) Assignee: VETCARE OY, Salo (FI)

( * ) Notice: Subject to any disclaimer, the term of this patent is extended or adjusted under 35 U.S.C. 154(b) by 0 days.

(21) Appl. No.: 15/525,382

(22) PCT Filed: Nov. 9, 2015

(86) PCT No.: PCT/FI2015/050774
§ 371 (c)(1),
(2) Date: May 9, 2017

(87) PCT Pub. No.: WO2016/075365
PCT Pub. Date: May 19, 2016

(65) Prior Publication Data
US 2017/0348291 A1    Dec. 7, 2017

(30) Foreign Application Priority Data
Nov. 10, 2014    (FI) .................................. 20145984

(51) Int. Cl.
| | | |
|---|---|---|
| *A61K 31/4375* | (2006.01) | |
| *A61K 31/4168* | (2006.01) | |
| *A61K 31/4174* | (2006.01) | |
| *A61K 31/426* | (2006.01) | |
| *A61K 31/54* | (2006.01) | |
| *A61K 9/00* | (2006.01) | |

(52) U.S. Cl.
CPC ...... *A61K 31/4375* (2013.01); *A61K 31/4168* (2013.01); *A61K 31/4174* (2013.01); *A61K 31/426* (2013.01); *A61K 31/54* (2013.01); *A61K 9/00* (2013.01)

(58) Field of Classification Search
CPC ................................................ A61K 31/4375
USPC ............................................................ 514/30
See application file for complete search history.

(56) References Cited

PUBLICATIONS

Enouri et al., "Effects of a peripheral $\alpha_2$ adrenergic-receptor antagonist on the hemodynamic changes induced by medetomidine administration in conscious dogs," American Journal of Veterinary Research, vol. 69, No. 6, Jun. 2008, pp. 728-736.
Finnish Search Report for Finnish Application No. 20145984, dated Jul. 2, 2015.
Honkavaara et al., "The effects of increasing doses of MK-467, a peripheral alpha$_2$-adrenergic receptor antagonist, on the cardiopulmonary effects of intravenous dexmedetomidine in conscious dogs," J. Vet. Pharmacol. Therap., vol. 34, 2010, pp. 332-337.
International Search Report and Written Opinion of the International Searching Authority (Forms PCT/ISA/210 and PCT/ISA/237) for International Application No. PCT/FI2015/050774, dated Feb. 9, 2016.
Pagel et al., "A Novel Alpha$_2$Adrenoceptor Antagonist Attenuates the Early, but Preserves the Late Cardiovascular Effects of Intravenous Dexmedetomidine in Conscious Dogs," Journal of Cardiothoracic and Vascular Anesthesia, vol. 12, No. 4, Aug. 1998, pp. 429-434.
Restitutti et al., "Effects of different doses of L-659'066 on the bispectral index and clinical sedation in dogs treated with dexmedetomidine," Veterinary Anaesthesia and Analgesia, vol. 38, 2011, pp. 415-422.
Rolfe et al., "Cardiopulmonary and sedative effects of the peripheral $\alpha_2$-adrenoceptor antagonist MK 0467 administered intravenously or intramuscularly concurrently with medetomidine in dogs," American Journal of Veterinary Research, vol. 73, No. 5, May 2012, pp. 587-594 (9 pages total).
Salla et al., "The cardiopulmonary effects of a peripheral alpha-2-adrenoceptor antagonist, MK-467, in dogs sedated with a combination of medetomidine and butorphanol," Veterinary Anaesthesia and Analgesia, vol. 41, Nov. 2014 (published online Mar. 27, 2014), pp. 567-574 (9 pages total).

*Primary Examiner* — Taofiq A Solola
(74) *Attorney, Agent, or Firm* — Birch, Stewart, Kolasch & Birch, LLP

(57) ABSTRACT

The present invention relates to compositions for facilitating absorption and distribution of $\alpha_2$-adrenergic agonists, where said composition comprises a substituted benzofuroquinolizine and a $\alpha_2$-adrenoceptor agonist selected from substituted imidazoles and substituted thiazines and the composition is administered using parenteral extravascular administration to a subject in need of sedation.

25 Claims, 3 Drawing Sheets

COMPOSITIONS COMPRISING SUBSTITUTED BENZOFUROQUINOLIZINE AND $\alpha_2$-ADRENERGIC AGONISTS

FIELD OF THE INVENTION

The present invention relates to compositions comprising a substituted benzofuroquinolizine known as MK-467 and $\alpha_2$-adrenergic agonists for use in sedation. The present invention also relates to a method for sedation using compositions comprising MK-467 and $\alpha_2$-adrenergic agonists for parenteral extravascular administration. The invention also relates to a method for enhancing absorption and distribution of $\alpha_2$-adrenergic agonists.

BACKGROUND OF THE INVENTION $\alpha_2$-adrenergic receptors are located on pre-junctional terminals in the central nervous system where they inhibit the release of norepinephrine in the form of negative feedback. They are further located postsynaptically on the vascular smooth muscle cells of certain blood vessels, such as those found in skin arterioles or on veins. The $\alpha_2$-adrenergic receptors bind both norepinephrine released by the sympathetic postganglionic fibers and epinephrine released by the adrenal medulla.

Common effects of $\alpha_2$-adrenergic receptors include suppression of release of norepinephrine by negative feedback, transient hypertension followed by sustained hypotension, decrease in heart rate, vasoconstriction of certain arteries, venoconstriction of some veins, decrease of motility of smooth muscles in the gastrointestinal tract, and sedation and analgesia.

Agonists (activators) of the $\alpha_2$-adrenergic receptors are frequently used as sedatives and in the anesthesia where they affect sedation, muscle relaxation and analgesia through effects on the central nervous system (CNS).

Substituted imidazoles and substituted thiazines are $\alpha_2$-adrenergic receptor agonists used in the veterinary medicine in sedation, analgesia and premedication, and in humans for similar purposes in intensive care. The activation of $\alpha_2$-adrenergic receptors located outside the CNS, such as postsynaptically located receptors on the vascular smooth muscle cells, induces vasoconstriction resulting in hypertension and significantly reduced heart rate, whereby the oxygen delivery to tissues is reduced.

The effect of substituted imidazoles and substituted thiazines is based on the activation of presynaptic $\alpha_2$-adrenergic receptors located in brains, which causes sedation, analgesia, and decrease of level of consciousness and fear.

Clonidine, romifidine, medetomidine, dexmedetomidine and detomidine are examples of such substituted imidazoles; xylazine is an example of substituted thiazines, useful as $\alpha_2$-adrenergic agonists.

Medetomidine, a rasemic mixture of dexmedetomidine and levomedetomidine, is a popular sedative and pre-anesthetic drug used in small animal practice. Medetomidine administration is associated with significant alterations in cardiovascular functions, such as dramatic increase in arterial blood pressure, in systemic and pulmonary vascular resistance, and in myocardial workload after IV administration. Further, reduction in heart rate and in cardiac output decrease global $Do_2$ (oxygen delivery) by at least 50%. Further adverse effects, such as vasoconstriction, bradycardia and decreased respiratory rate are typically caused by medetomidine. In some cases the level and quality of sedation and analgesia may not be sufficient and thus medetomidine may be combined with opioids, such as butorphanol, which has pure κ-agonist, partial μ-agonist and δ-agonist properties.

Dexmedetomidine, the pharmacologically active isomer of medetomidine, has similar side effects to medetomidine, such as vasoconstriction, acute $\alpha_2$-adrenoceptor agonist induced bradyarrhythmias and decreased respiratory rate. In dogs, both dexmedetomidine and medetomidine produce dose dependent degree of sedation, higher doses will prolong the sedative effects.

Detomidine is a $\alpha_2$-adrenergic agonist producing dose-dependent sedative and analgesic effects. Due to inhibition of the sympathetic nervous system it also has cardiac and respiratory effects and an antidiuretic action. After administration to a horse, short period of reduced coordination is characteristically followed by immobility and a firm stance with front legs spread. Following administration there is an initial increase in blood pressure, followed by bradycardia and second degree atrioventricular blocks. The horse commonly sweats to excess, especially on the flanks and the neck.

Detomidine is typically used for sedation and anesthetic premedication in horses and other large animals, commonly combined with butorphanol for increased analgesia and depth of sedation. It may also be used in conjunction with ketamine for intravenous anesthesia of short duration.

Further, re-sedation may occur, typically after 0.5-1 h after an animal has received a $\alpha_2$-adrenoceptor antagonist, such as atipamezole for reversing sedative effect of the $\alpha_2$-adrenoceptor agonist, such as medetomidine.

Several approaches have been studied to minimize the adverse effects of $\alpha_2$-adrenergic agonists, including the dose-dependency of the cardiovascular alterations and the effects of co-administration of anticholinergic agents.

IV administration of an experimental compound MK-467 (known also as L-659,066) has been suggested to attenuate the peripheral vascular effects of the $\alpha_2$-adrenergic agonists.

MK-467 overdose may cause adverse effects such as increase in the heart rate and cardiac index or reduction of blood pressure.

Effects of MK-467 on the hemodynamic changes induced by medetomidine administration in conscious dogs were studied in Enouri S et al, AJVR, Vol 69, No 6, (2008) 728-736. 0.2 mg/kg of MK-467 was administrated IV as pretreatment, and ten minutes after the administration the dogs received 10 μg/kg dose of medetomidine. Premedication with MK-467 prior to sedation with medetomidine reduced negative cardiovascular alterations induced by medetomidine administration in dogs.

Pagel P et al, J. Cardiothor. Vasc. Anaest., Vol 12, No 4, (1998) 429-434, describes premedication (IV) of dogs with 0.1, 0.2 and 0.4 mg/kg of MK-467, followed after 30 min by administration (IV) of 5 μg/kg dose of dexmedetomidine. MK-467 dose-dependently induced reduction in systemic vascular resistance coupled with an increase in heart rate and cardiac output, resulting in stable mean arterial pressures.

The effects of three doses of MK-467 (250, 500 and 750 μg/kg) in combination of 10 μg/kg of dexmedetomidine (IV) on bispectral index (BIS) and clinical sedation in dogs were evaluated in Restitutti F et al, Vet. Anaest. Analg. Vol 38, (2011) 415-422. BIS is used for monitoring sedation and loss of consciousness during anesthesia. Dexmedetomidine decreased BIS-values and MK-467 increased BIS-values especially with higher doses.

Influence of different doses of MK-467 on plasma concentrations of dexmedetomidine in dogs were evaluated in Honkavaara J et al, J Vet. Pharmacol. Therap. (2011) 38, 332-337. Dexmedetomidine 10 µg/kg with 250, 500 or 750 µg/kg and MK-467 (IV) were used. MK-467 dose-dependently attenuated dexmedetomidine induced increase in systemic vascular resistance and blood pressure and the consequent reductions in heart rate and cardiac index.

Cardiopulmonary effects of MK-467 in dogs sedated with medetomidine and butorphanol via IV and IM administration was studied in Salla K et al, Vet. Anaest. Analg. (2014) doi:10.1111/vaa.12158. MK-467 attenuated the cardiovascular effects of medetomidine-butorphanol combination after IV and IM administration.

Intravenous administration of sedative drugs may be a challenge to fractious or uncooperative animals. Thus, in many cases it is preferable to administer sedatives intramuscularly.

Medetomidine is used as sedative or pre-medicament in small animal medicine, and it can be administered intravenously, intramuscularly and subcutaneously (SC). When compared to IV administration, in IM or SC administration of medetomidine it typically takes more time before the sedation of the animal is sufficient for starting the procedure, operation etc. due to the need of absorption of active ingredients to circulation. It takes more of the veterinary's time and less patients can be treated daily. The problem is similar with other substituted imidazoles and substituted thiazines.

Rolfe et al, AJVR, 73(5), (2012) 587-94, describes the use 20 µg/kg of medetomidine, IM, alone or concurrently with MK-467 (0.4 mg/kg, IM), and 10 µg of medetomidine/kg, IV, alone or concurrently with MK-467 (0.2 mg/kg, IV), in dogs in a randomized crossover study. Concurrent administration was carried out in separate syringes at different locations. Heart rate (HR), mixed-venous partial pressure of oxygen (Pvo(2)), and cardiac index (CI) were significantly lower and mean arterial blood pressure (MAP), systemic vascular resistance (SVR), and oxygen extraction ratio (ER) were significantly higher after administration of medetomidine IM or IV, compared with baseline values. Administration of medetomidine and MK-467 IM caused a significantly higher heart rate, CI, and Pvo(2) and significantly lower MAP, SVR, and ER for 60 to 90 minutes than did IM administration of medetomidine alone. Administration of medetomidine and MK-467 IV caused a significantly higher CI and Pvo(2) and significantly lower MAP, SVR, and ER for 45 to 90 minutes than did IV administration of medetomidine alone. No significant difference in sedation was noticed.

Parenteral extravascular administration is commonly used in administration of sedatives in animals. However, it typically takes more time before the full sedative effect is reached than after IV route, which also increases the total time needed for carrying out the desired operation or procedure. Further, it also takes more time before the subject is recovered from the sedation.

SUMMARY OF THE INVENTION

An object of the invention is to provide a method for enhancing and/or facilitating absorption and distribution of $\alpha_2$-adrenergic agonists in a subject in need of treatment, such as sedation.

Another object of the invention is to provide use of MK-467 for enhancing and/or facilitating absorption and distribution of $\alpha_2$-adrenergic agonist, after parenteral extravascular administration to a subject in need of treatment, such as sedation.

Another object of the invention is to provide compositions comprising MK-467 and $\alpha_2$-adrenergic agonists for parenteral extravascular administration to a subject in need of treatment, such as sedation.

Still another object of the invention is to provide a method for enhancing and/or facilitating absorption and distribution of $\alpha_2$-adrenergic agonist after parenteral extravascular administration to a subject in need of treatment, such as sedation.

Still another object of the invention is to provide compositions comprising MK-467 and $\alpha_2$-adrenergic agonist for parenteral extravascular administration to a subject in need of treatment, such as sedation, with improved efficacy and safety.

Still another object of the invention is to provide an improved method for sedation of a subject, where the absorption and distribution of $\alpha_2$-adrenergic agonists is enhanced and/or facilitated.

The present invention relates to the use of MK-467 for enhancing and/or facilitating absorption and distribution of $\alpha_2$-adrenergic agonists after parenteral extravascular administration a compositions comprising MK-467 and $\alpha_2$-adrenergic agonist selected from substituted imidazoles and substituted thiazines to a subject in need of sedation.

Particularly the present invention relates to compositions comprising MK-467 and a $\alpha_2$-adrenergic agonist selected from substituted imidazoles and substituted thiazines for use in sedation, whereby absorption and distribution of $\alpha_2$-adrenergic agonists is enhanced and/or facilitated after parenteral extravascular administration of the composition to a subject in need of sedation.

The present invention also relates to a method for sedation of a subject, where a composition comprising MK-467 and $\alpha_2$-adrenergic agonist selected from substituted imidazoles and substituted thiazines is administered to a subject in need of sedation, using parenteral extravascular administration.

The present invention also relates to a method for sedation a subject, where a composition comprising MK-467 and a $\alpha_2$-adrenergic agonist selected from substituted imidazoles and substituted thiazines is administered to the subject using parenteral extravascular administration, followed by reversing the sedation by administering $\alpha_2$-adrenoceptor antagonist to the subject.

Characteristic features of the invention are presented in the appended claims.

Definitions

The term "$\alpha_2$-adrenoceptor agonists" refers here to $\alpha_2$-adrenergic receptor agonists, which are used for affecting sedation.

The term "sedation" refers here to calming through effects on the central nervous system (CNS), and it includes here tranquillization, immobilization, muscle relaxation and analgesia.

The term "$\alpha_2$-adrenoceptor antagonist" refers here to compounds useful in the prevention and/or reversing the effects of $\alpha_2$-adrenoceptor agonists.

The expression "parenteral extravascular administration" refers here to administration by the intramuscular route (IM), subcutaneous route (SC), transdermal route, and transmucosal route.

The expression "subject" refers here to humans and animals.

The expression "intramuscular route" refers here to administration of the substance into a muscle, typically using injections.

The expression "subcutaneous route" refers here to administration of the substance into the subcutis, which is the layer of skin directly below the dermis and epidermis, typically using injections.

The expression "transdermal route" refers here to administration of a substance by diffusion through the intact skin, typically using transdermal patches, gels etc.

The expression "transmucosal route" refers here to administration of the substance by diffusion through a mucous membrane, typically as sublingual, sublabial, rectal or intravaginal preparations.

DETAILED DESCRIPTION OF THE INVENTION

Figure 1:
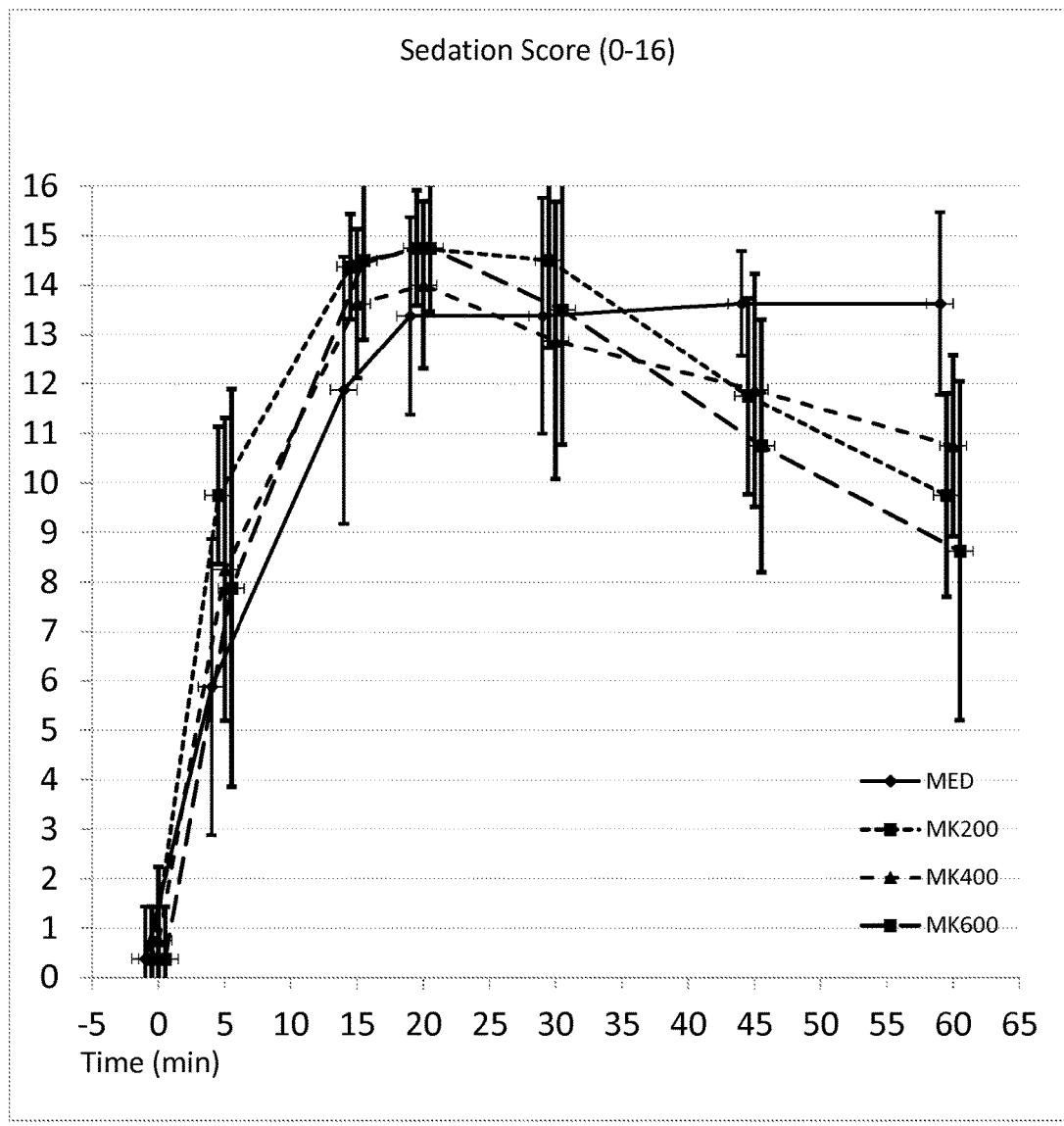
FIG. 1 presents sedation scores (mean±SD) of beagle dogs (n=8), treated IM with medetomidine 20 μg/kg (MED), medetomidine 20 μg/kg+MK-467 200 μg/kg (MK200), medetomidine 20 μg/kg+MK-467 400 μg/kg (MK400) and medetomidine 20 μg/kg+MK-467 600 μg/kg (MK600) mixed in the same syringe.

It was surprisingly found that after parenteral extravascular administration of a composition comprising MK-467 and $\alpha_2$-adrenoceptor agonist to a subject in need of treatment, particularly sedation, the absorption rate and the speed of distribution of the $\alpha_2$-adrenoceptor agonist is increased. With the invention the development of sedative effect was accelerated even four fold when compared with administration of the $\alpha_2$-adrenoceptor agonist without MK-467. Particularly the composition consists of MK-467, a $\alpha_2$-adrenergic agonist selected from substituted imidazoles and substituted thiazines, pharmaceutically acceptable carriers and pharmaceutically acceptable excipients and the composition is administered using parenteral extravascular administration to a subject in need of sedation.

The treatment refers particularly to sedation, and it includes tranquillization, immobilization, muscle relaxation, analgesia, and premedication.

The active compounds MK-467 and $\alpha_2$-adrenoceptor agonist are administered in one composition, locally, at the same time and to the same site of administration, whereby surprisingly fast absorption and distribution are achieved. MK-467 is effective after parenteral extravascular administration, when combined to a drug having its actions via $\alpha_2$-adrenoceptors including $\alpha_2$-adrenoceptor agonists, which are used for treating an animal species for sedation, including tranquillization, immobilization, analgesia, and premedication. MK-467 acts as $\alpha_2$-adrenoceptor antagonist on postsynaptically located receptors on the vascular smooth muscle cells. The adverse effects of $\alpha_2$-adrenoceptor agonists can be reduced or even avoided after parenteral extravascular administration of the composition comprising MK-467 and $\alpha_2$-adrenoceptor agonist to a subject.

MK-467 is also effective when used with other $\alpha_2$-adrenoceptor antagonists which are used to prevent and/or reverse the effects of any alpha-2 adrenoceptor agonists in an animal species. It was surprising found that effects of alpha-2 adrenoceptor agonists (induced by the composition of the invention) can be rapidly reversed, after an operation or procedure is finished or it is desirable for another reason to reverse the effects, by administering the $\alpha_2$-adrenoceptor antagonists to the subject, preferably by IM administration.

The present invention relates to the use of MK-467 for enhancing and/or facilitating absorption and distribution of $\alpha_2$-adrenergic agonist, where a composition comprising MK-467 and a $\alpha_2$-adrenergic agonist selected from substituted imidazoles and substituted thiazines is administered using parenteral extravascular administration to a subject in need of sedation.

According to another embodiment the present invention is directed to a composition comprising MK-467 and a $\alpha_2$-adrenergic agonist selected from substituted imidazoles and substituted thiazines for use in sedation, where the composition is administered using parenteral extravascular administration to a subject in need of sedation.

According to another embodiment the present invention is directed to a composition comprising MK-467 and a $\alpha_2$-adrenergic agonist selected from substituted imidazoles and substituted thiazines for use in sedation, where the composition is administered using parenteral extravascular administration to a subject in need of sedation, and $\alpha_2$-adrenoceptor antagonist is administered to the subject for use in reversing the sedation.

According to another embodiment the present invention relates to a method for sedation, where a composition comprising MK-467 and $\alpha_2$-adrenergic agonist selected from substituted imidazoles and substituted thiazines is administered to a subject in need of sedation, using parenteral extravascular administration.

The present invention also relates to a method for sedation, where a composition comprising MK-467 and a $\alpha_2$-adrenergic agonist selected from substituted imidazoles and substituted thiazines is administered to the subject using parenteral extravascular administration, followed by reversing the sedation by administering $\alpha_2$-adrenoceptor antagonist to the subject. In this embodiment the method for sedation includes sedation and reversing of sedation.

The composition of the invention is administered to a subject to provide a prescribed or approved dosage of the $\alpha_2$-adrenoceptor agonist. The dosage of the $\alpha_2$-adrenoceptor agonist depends of compound which is used and on the subject which receives treatment. Any doses of the $\alpha_2$-adrenoceptor agonist which are used to treat humans or any domestic or wild animal species are suitable.

The subject is selected from humans and animals. The animals are understood to mean vertebrate animal species selected from domestic animals and wild animals, including mammals, fish, birds, and reptiles. Examples of said animals are wild animals, animals kept is parks and zoos, laboratory animals, pets and livestock. The domestic animals include dogs, cats, rodents, reptiles, birds and other pets, horses, donkeys, pigs, bovine animals, sheep, goats, poultry, fish etc.

According to still another embodiment the present invention is directed to a method for enhancing and/or facilitating absorption and distribution of $\alpha_2$-adrenergic agonist, where a composition comprising MK-467 and a $\alpha_2$-adrenergic agonist is administered using parenteral extravascular administration to a subject in need of treatment.

MK-467 refers here to a peripherally acting α₂-adrenoceptor antagonist, known also by code as L-659,066. MK-467 has the following systematic chemical name N-[2-[(2R,12bS)-2'-oxospiro[1,3,4,6,7,12b-hexahydro-[1]benzofuro[2,3-a]quinolizine-2,5'-imidazolidine]-1'-yl]-ethyl]-methanesulfonamide (IUPAC). It is a spirocyclic substituted benzofuroquinolizine having the chemical formula I:

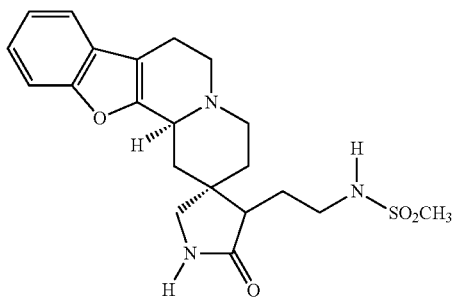

I

The composition of the invention is administered to a subject to provide a dosage of 1-5000 µg/kg of MK-467, preferably 10-3000 µg/kg of MK-467, particularly preferably 50-1500 µg/kg of MK-467.

The α₂-adrenoceptor agonist is selected from peripherally acting α₂-adrenoceptor agonists. Suitable α₂-adrenoceptor agonists are substituted imidazoles and substituted thiazines.

Preferably the α₂-adrenoceptor agonist is medetomidine ((RS)-4-[1-(2,3-dimethylphenyl)ethyl]-3H-imidazole of formula II), dexmedetomidine ((S)-4-[1-(2,3-Dimethylphenyl)ethyl]-3H-imidazole of formula III), detomidine (4-[(2,3-dimethylphenyl)methyl]-3H-imidazole of formula IV), romifidine (N(2-bromo-6-fluorophenyl)-4,5-dihydro-1H-imidazol-2-amine of formula V, clonidine (N-(2,6-dichlorophenyl)-4,5-dihydro-1H-imidazol-2-amine of formula VI) or xylazine (N-(2,6-dimethylphenyl)-5,6-dihydro-4H-1,3-thiazin-2-amine of formula VII), which are all structurally similar to each other. Particularly preferably the α₂-adrenoceptor agonist is detomidine, medetomidine, dexmedetomidine, romifidine or xylazine. Also any pharmaceutically acceptable salts of said compounds may be used in the invention.

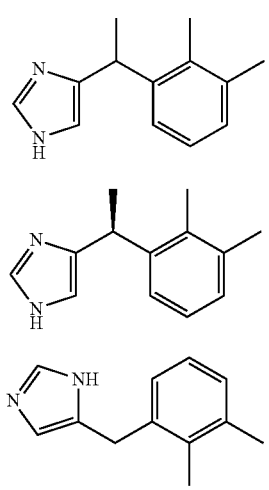

II

III

IV

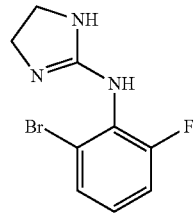

V

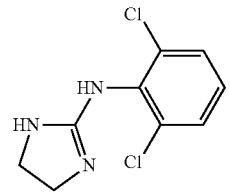

VI

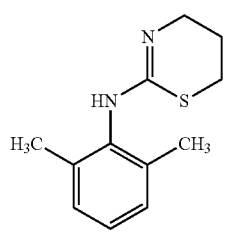

VII

The dosage of detomidine is suitably 0.1-5000 µg/kg, preferably 0.2-3000 µg/kg, particularly preferably 0.5-1000 µg/kg.

The dosage of medetomidine is suitably 0.1-5000 µg/kg, preferably 0.2-3000 µg/kg, particularly preferably 0.5-1000 µg/kg.

The dosage of dexmedetomidine is suitably 0.05-3000 µg/kg, preferably 0.1-2000 µg/kg, particularly preferably 0.1-1000 µg/kg.

The dosage of romifidine is suitably 0.1-5000 µg/kg, preferably 0.2-3000 µg/kg, particularly preferably 0.5-1500 µg/kg.

The dosage of clonidine is suitably 0.1-5000 µg/kg, preferably 0.2-3000 µg/kg, particularly preferably 0.5-1000 µg/kg.

The dosage of xylazine is suitably 1-20000 µg/kg, preferably 10-10000 µg/kg, particularly preferably 50-5000 µg/kg.

According to the invention both compounds MK-467 and the α₂-adrenoceptor agonist are administered at the same time, in the same composition, to the same administration site of the subject, using parenteral extravascular administration. Particularly the composition consists of MK-467, a α₂-adrenergic agonist selected from substituted imidazoles and substituted thiazines, pharmaceutically acceptable carriers and pharmaceutically acceptable excipients and the composition is administered using parenteral extravascular administration to a subject in need of sedation.

Preferably the administration of the composition is carried out by the intramuscular route (IM), subcutaneous route (SC), transdermal route, or transmucousal route.

Composition

Examples of the compositions of the invention, for parenteral extravascular administration, comprise solutions for intramuscular use and subcutaneous use (IM and SC solutions); gels, sprays, ointments, creams and patches for transdermal use (transdermal gels, sprays, ointments, creams and patches); and gels, ointments, creams, sprays and suppositories for transmucousal use (transmucousal gels, ointments, creams, sprays and suppositories). Transmucousal use includes here also sublingual and intravaginal administration.

Solutions for intramuscular (IM) and subcutaneous (SC) use may comprise saline or another physiologically acceptable aqueous medium, where MK-467 and the $\alpha_2$-adrenoceptor agonist are dissolved to desired concentrations. Pharmaceutically acceptable excipients, such as solubility and stability enhancing agents and preservatives, known in the art may be added if necessary to the composition.

For example, the IM or SC composition may comprise 0.1-500 mg/ml of MK-467 and 0.01-500 mg/ml of the $\alpha_2$-adrenoceptor agonist and a suitable preservative. Sterile solutions for intramuscular (IM) and subcutaneous use may be packed in any vials, bottles, syringes etc devices or containers known in the art.

Compositions for transdermal use may comprise one or more pharmaceutically acceptable carriers, supports, MK-467 and the $\alpha_2$-adrenoceptor agonist in dissolved state in a pharmaceutically acceptable medium, and excipients, including preservatives known in the art, depending whether the compositions is in the form of a gel, spray, cream, ointment or patch etc.

For example, the transdermal composition may comprise 0.1-1000 mg/ml of MK-467 and 0.01-500 mg/ml of the $\alpha_2$-adrenoceptor agonist.

Compositions for transmucousal use may comprise one or more pharmaceutically acceptable carriers, MK-467 and the $\alpha_2$-adrenoceptor agonist in dissolved state in a pharmaceutically acceptable medium, and excipients including preservatives known in the art, depending whether the compositions is in the form of a gel, spray, ointment or cream etc.

For example an oromucosal gel for sublingual use may comprise 0.1-1000 mg/ml of MK-467 and 0.01-100 mg/ml of the $\alpha_2$-adrenoceptor agonist, dissolved in an aqueous carrier, optionally with solubility enhancing agent(s) and surfactant(s), where said composition is formed to a gel with a gelforming agent, such as hydroxypropylcellulose or the like.

Reversing of Effects of $\alpha_2$-Adrenoceptor Agonist

As a further advantage of the invention it was surprisingly found that when a $\alpha_2$-adrenoceptor antagonist, other than MK-467, was used for reversing the central and peripheral effects of the $\alpha_2$-adrenoceptor agonist after administration of the composition of the invention to a subject, such as an animal, the recovery of the subject takes place more smoothly and rapidly because MK-467 also enhances distribution and absorption of said $\alpha_2$-adrenoceptor antagonists, which in turn facilitates the elimination of the $\alpha_2$-adrenoceptor agonist.

$\alpha_2$-adrenoceptor antagonists, other than MK-467, are used to prevent and/or reverse the effects of $\alpha_2$-adrenoceptor agonists. $\alpha_2$-adrenoceptor antagonists useful for reversing effects of substituted imidazoles and substituted thiazines are selected from a group consisting of idazoxan, tolazoline, yohimbine, rauwolskine, atipamezole, mirtazapine and (±)-2-methyl-1,2,3,4,10,14b-hexahydropyrazino[2,1-a]pyrido[2,3-c][2]benzazepine. In a preferable embodiment atipamezole is used.

Said $\alpha_2$-adrenoceptor antagonists are administered using parenteral extravascular administration, suitably using IM or SC administration. The dosage of the $\alpha_2$-adrenoceptor antagonists is generally from 10 to 1000 µg/kg, depending on the subject and the $\alpha_2$-adrenoceptor agonist used. Preferably IM administration is used.

Atipamezole is a specific $\alpha_2$-adrenoceptor antagonist, which is used commonly for reversing the central and peripheral effects of medetomidine and dexmedetomidine in animals.

The present invention provides several advantages to the subject and to the practitioner. The inventors have found that after parenteral extravascular administration of the composition comprising MK-467 and $\alpha_2$-adrenoceptor agonist to a subject, such as an animal, in need of sedation, the absorption rate and the speed of distribution of the $\alpha_2$-adrenoceptor agonist is increased even four fold when compared with administration of the $\alpha_2$-adrenoceptor agonist without MK-467. The onset of action of the $\alpha_2$-adrenoceptor agonist, particularly sedation starts more rapidly as can be seen from the examples. Long waiting periods can be avoided as less time is needed before an operation or procedure can be started. Further, the effects of the $\alpha_2$-adrenoceptor agonist are reversed faster due to the improved distribution and absorption of $\alpha_2$-adrenoceptor antagonists, the animal recovers more rapidly and long recovery periods after the operation or procedure can be avoided or at least decreased significantly.

The wellbeing of the animal is improved because of less side-effects, easier administration, faster induction and recovery when sedatives are used and shorter and smoother visits to the veterinarian. Also potential re-sedation after the reversing $\alpha_2$-adrenoceptor antagonist, such as atipamezole, induced recovery from sedation is inhibited by the invention and the composition comprising MK-467 and the $\alpha_2$-adrenoceptor agonist.

More patients can be treated with a period of time as long waiting periods can be avoided both in the onset of sedation and recovery, which increases the productivity of the veterinarian and brings economic advantages.

Further, as the onset of the sedative action is faster, potentially dangerous animals can be sedated without unnecessary delay, which also increases the safety of the veterinarian.

EXAMPLES

The invention will now be illustrated with the following examples and with reference to the drawings.

Example 1

Sedation of Dogs with Medetomidine+MK-467, IM Administration with One Composition The study was designed as a prospective, randomized, experimental cross-over study.

Each dog (n=8) received four different treatments with 14-days washout periods:
Medetomidine 20 µg/kg IM
Medetomidine 20 µg/kg+MK-467 200 µg/kg IM
Medetomidine 20 µg/kg+MK-467 400 µg/kg IM
Medetomidine 20 µg/kg+MK-467 600 µg/kg IM MK-467 was diluted immediately prior to administration with standard saline solution to a concentration of 10 mg/ml. Prior to the intramuscular injection, calculated doses of medetomidine (1 mg/ml) and MK-467 were separately aspirated into two syringes. The contents of both syringes were mixed in a third, separate, empty syringe.

Sedation was scored by a veterinarian blinded for treatment with the following score:
Composite Sedation Score (0-16)
1. Palpebral Reflex (0-3)
   0 Normal
   1 Slightly reduced
   2 Weak
   3 Absent 2. Position of the Eye (0-2)
   0 Middle
   2 Turned down
3. Jaw and Tongue Relaxation (0-4)
   0 Normal, opens the jaws but resists manipulation of the tongue
   1 Bites jaws together
   2 Opens the jaws but strong resistance when tongue is pulled
   3 Slight resistance when tongue is pulled
   4 No resistance
4. Resistance to Positioning in Lateral Recumbency (0-3)
   0 Normal
   1 Turns back to sternal position
   2 Some resistance but stays in lateral recumbency
   3 No resistance or the position is already lateral
5. General Appearance (0-4)
   0 Normal
   1 Slightly tired, head drooping
   2 Mild sedation, reacts clearly to surroundings
   3 Moderate sedation, reacts slightly to surroundings
   4 Deep sedation, no reaction to surroundings The concentrations of dexmedetomidine and levomedetomidine in plasma were determined with HPLC-MS/MS.

In FIG. 1 sedation scores (mean±SD) of beagle dogs (n=8), treated with medetomidine 20 µg/kg (MED), medetomidine 20 µg/kg+MK-467 200 µg/kg (MK200), medetomidine 20 µg/kg+MK-467 400 µg/kg (MK400) and medetomidine 20 µg/kg+MK-467 600 µg/kg (MK600) are shown. The drugs were mixed in the same syringe and administered intramuscularly at time 0 min. It can be seen that the onset of the sedation was faster and the maximum sedative effect was better with MK-467. FIG. 1 also shows that the dogs recovered faster from sedation when MK-467 was used concomitantly with the sedative drug.

Figure 2:
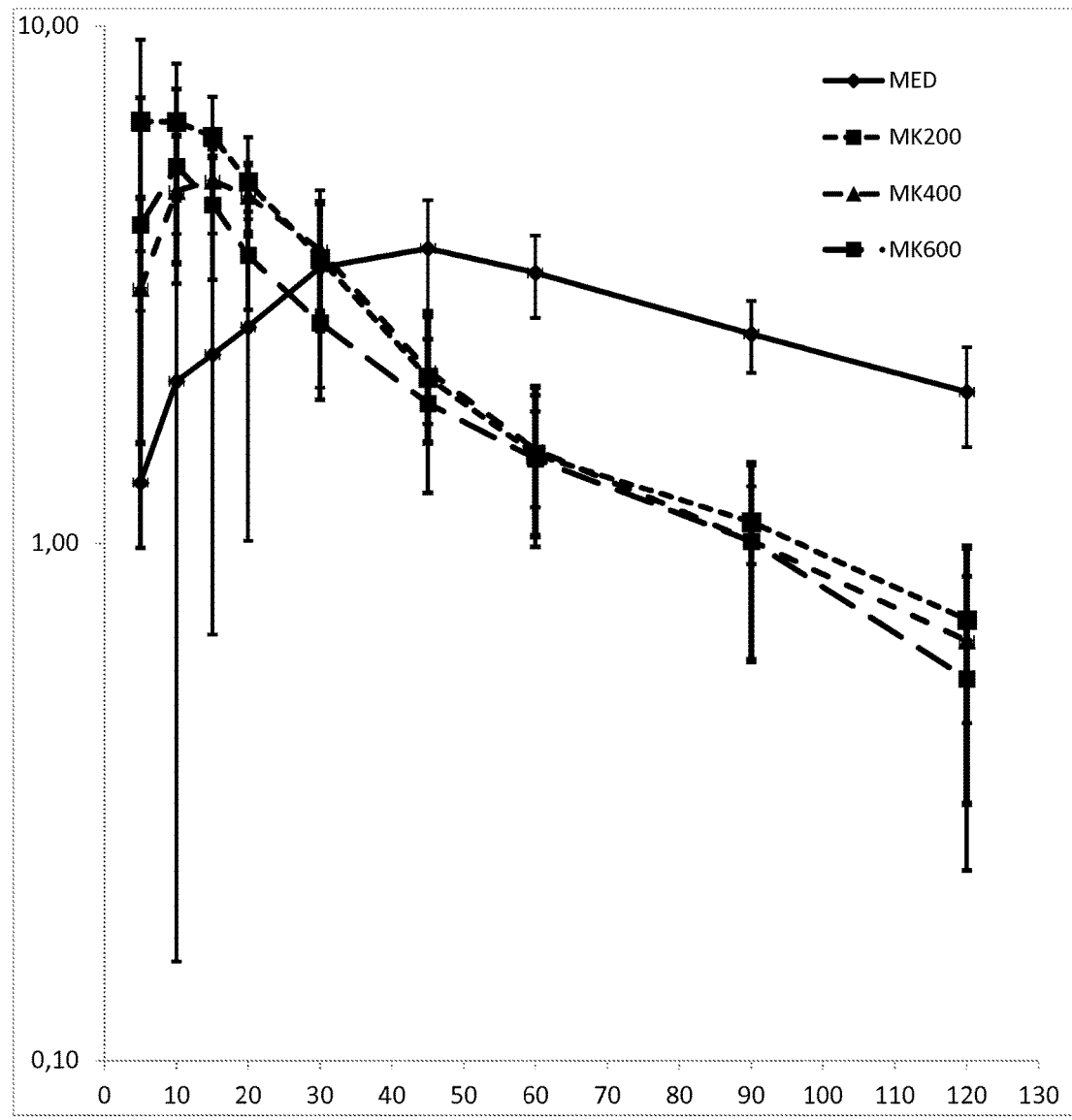
FIG. 2 presents plasma dexmedetomidine concentrations (mean±SD; ng/mL) of beagle dogs (n=8) treated IM with medetomidine 20 μg/kg (MED), medetomidine 20 μg/kg+MK-467 200 μg/kg (MK200), medetomidine 20 μg/kg+MK-467 400 μg/kg (MK400) and medetomidine 20 μg/kg+MK-467 600 μg/kg (MK600) mixed in the same syringe.

FIG. 2 shows plasma dexmedetomidine concentrations (mean±SD; ng/mL) measured during the same study as in FIG. 1. From FIG. 2 it can be concluded that the absorption of medetomidine was faster and the maximum plasma concentration was higher with MK-467, which explains the faster and deeper sedation seen in FIG. 1.

Example 2

Sedation with Medetomidine and MK-467 IM in One Composition, Followed by Reverse with Atipamezole The study was designed as a prospective, randomized, experimental cross-over study.

Each dog (n=7) was treated twice with a 14-days washout period:
   Medetomidine (20 µg/kg) at 0 min, followed by Atipamezole (100 µg/kg) at 30 min
   Medetomidine (20 µg/kg)+MK-467 (400 µg/kg) at 0 min, followed by Atipamezole (100 µg/kg) at 30 min Medetomidine and MK-467 were mixed in the same syringe and administered intramuscularly.

Figure 3:
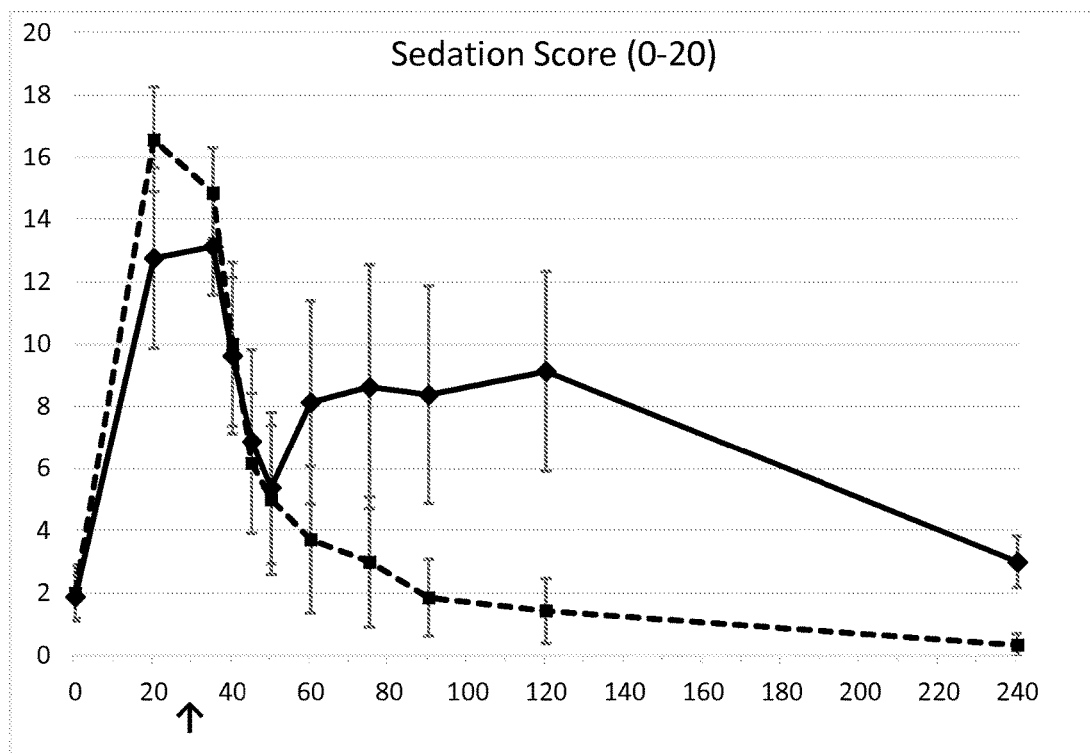
FIG. 3 shows sedation scores (mean±CI95%) of beagle dogs (n=7) treated with medetomidine (20 μg/kg IM, solid line), or medetomidine (20 μg/kg IM) and MK-467 (400 μg/kg IM) mixed in the same syringe (dotted line), at 0 min. Atipamezole (100 μg/kg IM) was administered at 30 min (arrow).

Sedation was scored by a veterinarian blinded for treatment with the following score:
Composite Sedation Score (0-20)
1. Position (0-4)
   0 Standing
   1 Standing but staggers
   2 Sternal head up
   3 Sternal head down
   4 Lateral head down
2. Palpebral Reflex (0-3)
   0 Normal
   1 Slightly reduced
   2 Weak
   3 Absent
3. Position of the Eye (0-2)
   0 Middle
   2 Turned down
4. Jaw and Tongue Relaxation (0-4)
   0 Normal, opens the jaws but resists manipulation of the tongue
   1 Bites jaws together
   2 Opens the jaws but strong resistance when tongue is pulled
   3 Slight resistance when tongue is pulled
   4 No resistance
5. Resistance to Positioning in Lateral Recumbency (0-3)
   0 Normal
   1 Turns back to sternal position
   2 Some resistance but stays in lateral recumbency
   3 No resistance or the position is already lateral
6. General Appearance (0-4)
   0 Normal
   1 Slightly tired, head drooping
   2 Mild sedation, reacts clearly to surroundings
   3 Moderate sedation, reacts slightly to surroundings
   4 Deep sedation, no reaction to surroundings In FIG. 3 the sedation scores (mean±CI95%) of dogs (n=7) treated with medetomidine (20 µg/kg IM, solid line), and medetomidine (20 µg/kg IM) and MK-467 (400 µg/kg IM) mixed in the same syringe (dotted line), at 0 min are presented. Atipamezole (100 µg/kg IM) was administered at 30 min (arrow). It can be seen that atipamezole reversed the medetomidine induced sedation when medetomidine was given alone or when given concomitantly with MK-467. However, when MK-467 was co-administered with medetomidine in the same syringe the resedation seen in dogs treated with medetomidine alone was prevented.

Example 3

Study with MK-467 and Detomidine when Administered as Oromucosal Gel in Sheep

The objective of the study is to evaluate the effect of MK-467 on the transmucosal absorption rate of detomidine when administered as oromucosal gel in sheep. The results will show that MK-467 incorporated in detomidine oromucosal gel increases the transmucosal absorption rate of detomidine, which will be detected by decreased time to maximum concentration ($T_{max}$) and increased maximum plasma concentration of detomidine ($C_{max}$).

Study design: Randomized, prospective, cross-over study with at least seven days wash-out period.

Animals: Three sheep

Methods: Each sheep will get two treatments:
   1. detomidine (50 µg/kg) oromucosal gel sublingually
   2. detomidine (50 µg/kg) oromucosal gel mixed with MK-467 (500 µg/kg) sublingually Blood will be collected at 5, 10, 15, 20, 25, 30, 40, 50 and 60 minutes after drug administration, and plasma drug concentrations will be analysed with liquid chromatography and tandem mass spectrometry (LC/MS/MS). Maximum plasma concentration of detomidine ($C_{max}$) and the time to maximum concentration ($T_{max}$) will be calculated from the plasma detomidine concentration-time data.

The present invention has been described herein with reference to specific embodiments. It is, however clear to those skilled in the art that the invention may be varied within the bounds of the claims.

The invention claimed is:

1. A composition for parenteral extravascular administration, comprising:
   MK-467,
   an $\alpha_2$-adrenoceptor agonist comprising at least one of medetomidine, dexmedetomidine, detomidine, romifidine, clonidine or xylazine, and
   one or more of physiologically acceptable aqueous media, pharmaceutically acceptable carriers and pharmaceutically acceptable excipients.

2. The composition according to claim 1, wherein the $\alpha_2$-adrenoceptor agonist is medetomidine, dexmedetomidine, detomidine, romifidine or xylazine.

3. The composition according to claim 1, wherein the composition is administered to a subject selected from humans and animals.

4. The composition according to claim 3, wherein the animals are vertebrates.

5. The composition according to claim 1, wherein the composition is administered to a subject to provide a dosage of 1-5000 μg/kg of MK-467 and 0.1-20000 μg/kg of the $\alpha_2$-adrenoceptor agonist.

6. The composition according to claim 1, wherein the composition is selected from solutions for intramuscular use and subcutaneous use; from gels, sprays, ointments, creams and patches for transdermal use; and from gels, ointments, creams, sprays and suppositories for transmucousal use.

7. The composition according to claim 1, wherein the composition comprises 0.1-1000 mg/ml of MK-467 and 0.01-500 mg/ml of the $\alpha_2$-adrenoceptor agonist.

8. The composition according to claim 1, wherein the composition is a solution for intramuscular use or subcutaneous use and it comprises 0.1-500 mg/ml of MK-467 and 0.01-500 mg/ml of the $\alpha_2$-adrenoceptor agonist.

9. The composition according to claim 1, wherein the composition is a gel, spray, ointment, cream or patch for transdermal use and it comprises 0.1-1000 mg/ml of MK-467 and 0.01-500 mg/ml of the $\alpha_2$-adrenoceptor agonist.

10. The composition according to claim 1, wherein the composition is a gel, ointment, cream, spray or suppository for transmucousal use and it comprises 0.1-1000 mg/ml of MK-467 and 0.01-100 mg/ml of the $\alpha_2$-adrenoceptor agonist.

11. A method for sedation, where a composition comprising MK-467, an $\alpha_2$-adrenoceptor agonist comprising at least one of medetomidine, dexmedetomidine, detomidine, romifidine, clonidine or xylazine, and one or more of physiologically acceptable aqueous media, pharmaceutically acceptable carriers and pharmaceutically acceptable excipientsis, is administered to a subject in need of sedation, wherein said administration is parenteral extravascular administration.

12. The method according to claim 11, wherein the $\alpha_2$-adrenoceptor agonist is medetomidine, dexmedetomidine, detomidine, romifidine or xylazine.

13. The method according to claim 11, wherein the subject is selected from humans and animals.

14. The method according to claim 11, wherein the animals are vertebrates.

15. The method according to claim 11, wherein the composition is administered to a subject to provide a dosage of 1-5000 μg/kg of MK-467 and 0.1-20000 μg/kg of the $\alpha_2$-adrenoceptor agonist.

16. The method according to claim 11, wherein the composition is selected from solutions for intramuscular use and subcutaneous use; from gels, sprays, ointments, creams and patches for transdermal use; and gels, ointments, creams, sprays and suppositories for transmucousal use.

17. The method according to claim 11, wherein the composition comprises 0.1-1000 mg/ml of MK-467 and 0.01-500 mg/ml of the $\alpha_2$-adrenoceptor agonist.

18. The method according to claim 11, wherein the composition is a solution for intramuscular use or subcutaneous use and it comprises 0.1-500 mg/ml of MK-467 and 0.01-500 mg/ml of the $\alpha_2$-adrenoceptor agonist.

19. The method according to claim 11, wherein the composition is a gel, spray, ointment, cream or patch for transdermal use and it comprises 0.1-1000 mg/ml of MK-467 and 0.01-500 mg/ml of the $\alpha_2$-adrenoceptor agonist.

20. The method according to claim 11, wherein the composition is a gel, ointment, cream, spray or suppository for transmucousal use and it comprises 0.1-1000 mg/ml of MK-467 and 0.01-100 mg/ml of the $\alpha_2$-adrenoceptor agonist.

21. A method for reversing sedation caused by the method according to claim 11, comprising:
   administering an $\alpha_2$-adrenoceptor antagonist comprising idazoxan, tolazoline, yohimbine, rauwolskine, atipamezole, mirtazapine, or (±)-2-methyl-1,2,3,4,10,14b-hexahydropyrazino[2,1-a]pyrido[2,3-c][2]benzazepine to the subject.

22. The composition according to claim 1, wherein the composition is administered to a wild animal or a domestic animal.

23. The composition according to claim 1, wherein the composition is administered to a mammal, a fish, a bird, or a reptile.

24. The method according to claim 11, wherein the subject is a wild animal or a domestic animal.

25. The method according to claim 11, wherein the subject is a mammal, a fish, a bird, or a reptile.

* * * * *